United States Patent [19]

Anathasubramanian et al.

[11] 4,415,498

[45] Nov. 15, 1983

[54] SYNTHESIS OF DAUNOMYCINONE AND THE DERIVATIVES THEREOF

[75] Inventors: Lakshminarayan Anathasubramanian, Brookline; T. Ross Kelly, Watertown; Jacob Vaya, Brookline, all of Mass.

[73] Assignee: Research Corporation, New York, N.Y.

[21] Appl. No.: 91,897

[22] Filed: Nov. 7, 1979

[51] Int. Cl.$^3$ .................. C07C 49/72; C07C 49/73
[52] U.S. Cl. .................. 260/351.1; 260/365
[58] Field of Search .................. 260/351.1, 365

[56] References Cited

U.S. PATENT DOCUMENTS 4,070,382  1/1978  Kende et al. .................. 260/365
4,302,398  1/1981  Hassall et al. .................. 260/365

OTHER PUBLICATIONS

*Tetrahedron Letters,* T. Ross Kelly, 1976, No. 43, pp. 3873–3876, "Studies Directed Toward the Synthesis of Adriamycin": A Diels–Alder Approach, Pergamon Press, GB.
*Justas Liebigs Annalen Der Chemie,* K. Krohn et al., 1979, Nos. 9–12, pp. 2018–2027, "Total Synthese des rac B.-Rhodomycinons".
*Chem. Ber.,* Krohn et al., 1979, vol. 113, pp. 2976–2993, "Synthese neuer Derivate des Daunomycinons und des B.-Rhodomycinons".
*Chem. Ber.,* Krohn et al., 1979, vol. 113, pp. 2640–2649, "Synthese von DL-4-Desmethoxy-7,10-ethanodaunomycinon".
*Chem. Ber.,* Krohn et al., 1979, vol. 112, pp. 3453–3471, "Total Synthese des Daunomycinons".
*Chem. Ber.,* Tolkiehn et al., 1980, vol. 113, pp. 1575–1583, "Regiosepktive Synthese von Digitopurpon und Islandicin durch Komibinierte Diels–Alder–und Marscholk–Renkiton".

*Primary Examiner*—Delbert E. Gantz
*Assistant Examiner*—Raymond Covington
*Attorney, Agent, or Firm*—Scully, Scott, Murphy & Presser

[57] ABSTRACT

Regio- and stereospecific method for the preparation of daunomycinone and derivatives thereof utilizing the p-nitrobenzyloxy carbonyl group as a blocking group.

16 Claims, No Drawings

SYNTHESIS OF DAUNOMYCINONE AND THE DERIVATIVES THEREOF

The invention described herein was made in the course of work under a grant or award from the Department of Health, Education and Welfare.

BACKGROUND OF INVENTION

During the past several years, the anthracyclines, most notably adriamycin, daunomycin and carminomycin have emerged as important chemotherapeutic agents because of their antimicrobial activity, and because of their activity against a broad spectrum of human cancers. The products are presently produced by fermentation. However, extensive efforts have been made to develop a totally synthetic route which would permit the practical production of the compounds by chemical means and also open the pathway for the production of potentially more useful analogs.

The efforts have principally been directed toward the preparation of adriamycinone, daunomycinone, carminomycinone and other sugar free analogs since procedures for the substitution of L-daunosamine at the seven positions of the anthracycline ring are well known. Such methods as have been developed however have been plagued with difficulty, principally due to the opportunities for the production of unwanted and inactive regio- or stereo isomers. As a result, the overall yields have been unacceptably low.

THE INVENTION

A method has now been discovered which makes possible the preparation of daunomycinone having the correct regio- and stereospecific configuration, and to do so in an overall yield of twenty-five percent. This compares with overall yields of less than ten percent for previously known methods.

For convenience, the process of this invention will be described principally as it relates to the preparation of daunomycinone and its 4-position homologs. It is also applicable to the preparation of related products such as adriamycinone, and known analogs. It is particularly useful for the preparation of D-ring analogs in which the 1-, 2- and 4-positions are substituted with alkyl or alkoxy groups containing, for example, up to five carbon atoms. In such compounds, all of these positions may be substituted with the same alkyl or alkoxy groups, different alkyl or alkoxy groups, or mixtures of these.

Daunomycinone and its homologs to which the process of this invention is particularly applicable may be represented by the formula:

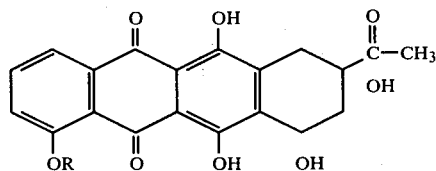

where R is an alkyl group containing up to five carbon atoms. The alkyl group may be either straight or branched.

In the balance of this description, R may be understood to always have the same meaning.

In the first step of the process naphthazarin is reacted with p-nitrobenzyloxy chloroformate to produce the p-nitrobenzyl carbonate derivative. The compound may be represented by the formula:

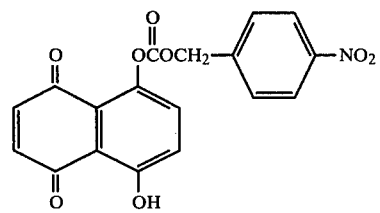

While an excess of either reagent may be employed, it is preferred to use equimolar quantities so as to limit contamination of the product. Reaction is effected at a temperature of from about 20° C. to 75° C. in the presence of a basic reagent, preferably an amine so as to neutralize the acid produced. Any of the usual aliphatic or aromatic tertiary amine scavengers can be employed including tributyl amine, dimethyl aniline or diethyl aniline. The presently preferred neutralizing reagent is triethyl amine.

One procedure is, initially, to react naphthazarin with 0.5 eq. of the acide halide in the selected solvent, precipitate the product by the addition of a precipitating solvent, add an additional 0.5 eq. of acide halide, and finally produce the remainder of the product by the addition of additional precipitating solvent.

Another is to react equimolar quantities of the reactants as illustrated in the examples. If this procedure is employed, the reaction period is about 6 to 12 hours. If the procedure utilizing half molar amounts of acid halide is employed, the reaction time is doubled.

Any of a variety of solvent pairs can be employed. Generally, the precipitating reagent is less polar than the reaction solvent. The presently preferred reaction pair is toluene and petroleum ether.

The next step is to utilize the Diels Alder reaction to substitute the ring which ultimately becomes the D-ring of the daunomycinone. The product is represented by the formula:

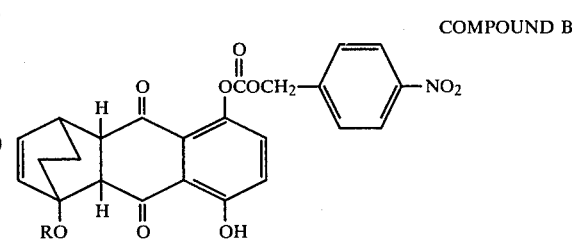

COMPOUND B

The reaction conditions are typical Diels Alder conditions employing a non-polar organic solvent at about 20° C. to 40° C. for a period of from about 3 to 8 hours. Typically useful solvents include methylene chloride, chloroform, benzene, toluene and other aliphatic and aromatic hydrocarbon and halogenated hydrocarbon solvents.

The adduct may be isolated by precipitation with a nonsolvent.

Oxidation or dehydrogenation of Compound B in the presence of a non-neucleophilic strong base such as sodium or potassium hydride or an alkali metal t-butoxide produces Compound C.

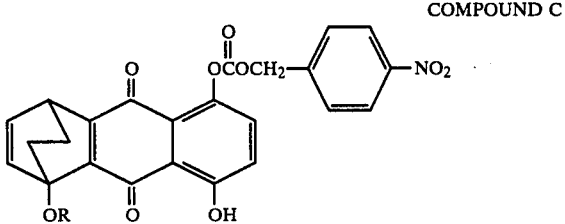

COMPOUND C

The postulated mechanism of the reaction is that the hydrogens at the ring junction are initially replaced with alkali metal and then removed with the oxidizing agent.

In carrying out the reaction, the strong base is added to the substrate which is dissolved in an ether solvent, typically tetrahydrofuran, (THF) at a low temperature, for example −10° C. to 10° C. The oxidizing agent is added and the mixture stirred at about the same temperature for 2 to 5 hours to produce the desired product.

The presently preferred oxidizing agents are mild oxidizing agents such as lead or silver oxides. Neither dissolve in the reaction medium. They are removed at the end of the reaction and the dissolved product recovered.

It should be mentioned that Compound C exists in equilibrium with Compound C'. There is, however, no necessity for isolating either of them since the mixture reacts as though it was all Compound C' to produce Compound D as described below. Compound C' may be represented by the formula:

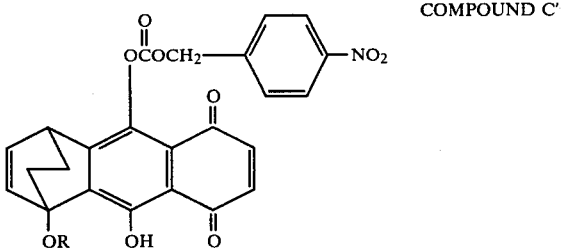

COMPOUND C'

The next reaction is a Diels Alder reaction to produce Compound D, a compound with the A-ring of the final anthracycline compound in place. Compound D may be represented by the formula:

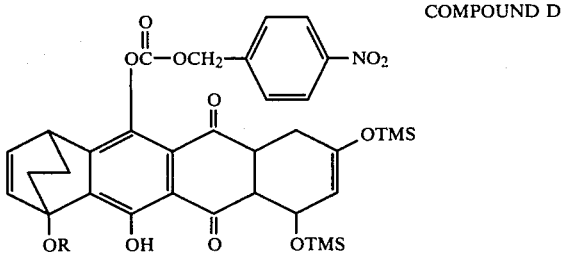

COMPOUND D wherein TMS represents the trimethylsilyl group.

The reaction conditions are as described above except that in general, the reaction is carried out for a slightly longer period. The diene employed is 1,3 bis(-trimethylsilyloxy)-1,3-butadiene.

The products represented by the formula of Compound D are in the correct regiochemical configuration. This configuration was controlled by the directing influence of the p-nitrobenzyloxy carbonyl group during the Diels Alder reactions. In the first Diels Alder reaction, the alkoxyl group of Compound B is on the opposite side of the structure from the protecting group, as shown above. In the second Diels Alder, the trimethylsilyloxy substituent at the position adjacent the A, B-ring juncture is also on the opposite side of the structure from the protecting group as shown in Compound D.

There is, however, a mixture of sterioisomers arising principally from the centers of asymmetry at the 1, 4, 6a and 10a positions on the D-ring and at the juncture of the A- and the B-ring. The existence of these sterioisomers does not present a particular problem since they are destroyed upon aromatization of Ring D and oxidation of the A, B-ring juncture.

While the p-nitrobenzyl group is presently preferred, the o-nitro benzoyl group is also useful as a protecting and directing group.

The next step is the production of Compound E:

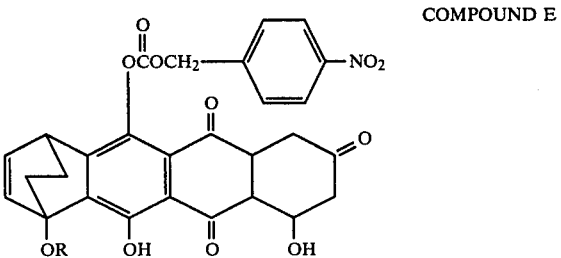

COMPOUND E by hydrolytic removal of the trimethylsilyloxy groups.

Hydrolysis is effected within aqueous mineral acid, preferably dilute acid such as 3N HCl. The group adjacent the double bond is extremely labile and may be removed with acid alone. The other trimethylsilyloxy group is more stable. Its removal is facilitated, however, by the addition of 30% hydrogen peroxide. A small amount of solvent ether or ketone solvent such as THF or acetone assists the reaction by dissolving the substrate.

The reaction time is usually 0.5 to one hour. The time can be controlled by the amounts of solvent or reagents employed. Generally, the time increases with increasing amounts of solvent or with decreasing amounts of reagent.

The reaction temperature is from about −5° C. to 5° C.

If desired, an intemediate compound,, represented by the formula

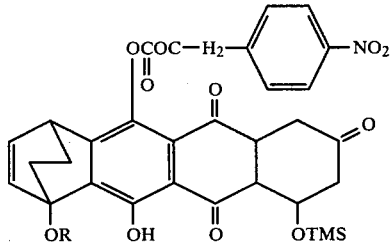

can be isolated, but there is no particular advantage in doing so.

The next step is removal of the blocking group to produce Compound F, represented by the formula:

COMPOUND F

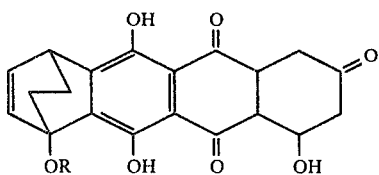

COMPOUND I

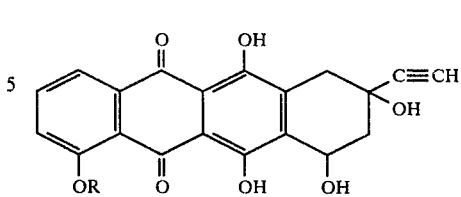

This reaction is effected by reduction of the nitro group to an amine under mild reducing conditions. The resulting anilino substituent is unstable and under the conditions of the reaction, spontaneously decomposes to leave an hydroxyl substituent.

The presently preferred reducing agent is Zn/ acetic acid. This reagent is preferred since it does not aromatize the A-ring or affect the unsaturation in the D-ring.

The reaction is carried out at about −10° C. to 10° C. during a period of about 2 minutes to 2 hours. Reaction is facilitated by the use of a solvent, particularly an ether or ketone solvent such as THF or acetone. The solvent assists in dissolving the substrate and also permits the use of liquid acetic acid at a temperature below its normal freezing point. The solvent is not essential.

The Grignard reaction followed by oxidation is used to produce compounds G and H. These compounds are represented by the formulas:

COMPOUND G

COMPOUND H

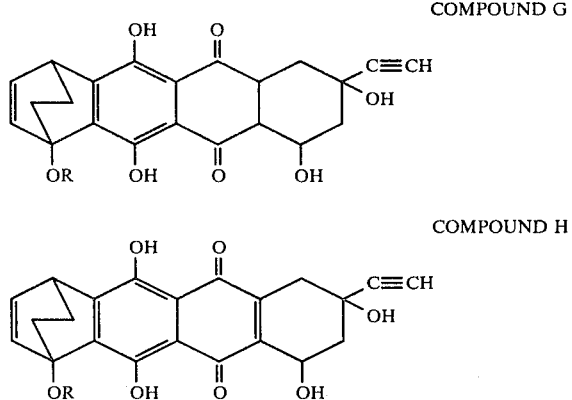

The Grignard reaction is carried out under standard Grignard conditions in a solvent at about −10° C. to 10° C. for a period of from about 1 to 3 hours. The reaction is quenched with dilute tartaric acid or equivalent such as oxalic or hydrochloric acid.

Oxidation of the ring juncture of the A- and B-ring is effected with aqueous base in a solvent such as THF. Suitable bases include 2.5% sodium hydroxide or saturated aqueous sodium bicarbonate. The reaction period is from about 0.5 to 2 hours at a temperature of from about −10° C. to 10° C.

The D-ring is converted to an aromatic ring by heating for from about 0.25 hour to one hour at from about 130° C. to 180° C. It is not necessary to use a solvent, but it is preferred to do so. It should be a high boiling inert solvent such as xylene. The compound produced, Compound I, is represented by the formula:

Hydration of Compound I with mercuric sulfate and aqueous sulfuric acid in a reaction inert organic solvent such as acetone or THF at about 20° C. to 40° C. for about 10 to 20 hours produces daunomycinone.

Actually a mixture of two sterioisomers including the unnatural 7-epi compound is produced. The principal component is the natural product. This mixture is readily converted to the predominantly natural form by treatment with trifluoroacetic acid according to known methods.

It should be mentioned that sterioisomers produced in the course of the reaction sequence described herein can be isolated if desired. They have in fact been isolated and characterized to establish with certainty the course of the synthesis.

The following non-limiting examples are given by way of illustration only.

EXAMPLE I

P-NITROBENZYL CARBONATE OF NAPHTHAZARIN

COMPOUND A

Naphthazarin (6 g.) was dissolved in 550 ml of a 1:1 mixture of toluene and petroleum ether and stirred mechanically at 40° C. One equivalent of triethylamine and p-nitrobenzyloxy chloroformate in 25 ml of THF were added in portions over a period of 3 hours. The precipitated compound was filtered and washed with petroleum ether to remove naphthazarin. The remaining solid was saturated with EtOAc and the extract concentrated to a solid (6.9 g). This solid was recrystallized several times from toluene to separate the monoprotected compound from the di-protected one. The sample was crystallized from ethyl acetate m.p. 185°–186° C.

EXAMPLE II

1-METHOXY-1,3 CYCLOHEXADIENE ADDUCT OF COMPOUND A

COMPOUND B

The mono-protected product of the previous example (6 g) was dissolved in 750 ml of dry methylene chloride and 1.5 eq. of 1-methoxy-1,3 cyclohexadiene was added. The reaction mixture was left overnight stirring under nitrogen. The completion of the reaction was checked by thin layer chromatography (TLC) and the solvent evaporated in vacuo. The remaining viscous oil was stirred with petroleum ether for several hours to remove the excess diene whereupon the product precipitates (7 g). It was filtered and recrystallized from ethyl acetate; m.p. 148°–149° C.

EXAMPLE III

OXIDATION OF COMPOUND B

COMPOUND C

The unoxidized tricycle (3.21 g) of the previous example was dissolved in 200 ml of dry THF, and to this one equivalent of dry KH suspension in THF was added at −70° C. After 30 minutes, 5 gr. of lead dioxide was added, the reaction temperature spontaneously increased to 0° C. The progress of the reaction was monitored by TLC and, after completion, was poured into phosphate buffer at pH4 at 0° C., extracted with methylene chloride, washed with water and dried to yield 3.1 g of product. The product was recrystallized from ether/ethyl acetate. It was characterized spectrographically and by analytical analysis. Significant NMR; delta (CDCl$_3$); 12.75(1H, S,OH); 6.5 (2H,M, vinylic H); 3.68 (3H,S,OCH$_3$).

EXAMPLE IV

1,3-BIS(TRIMETHYLSILYLOXY)-1,3-BUTADIENE ADDUCT OF COMPOUND C

COMPOUND D

The product of the previous example (2 g) was dissolved in 100 ml of dry methylene chloride and 2 eq. of diene was added. The reaction mixture was stirred for forty-eight hours under N$_2$. The completion of the reaction was checked by TLC. The yield is quantative.

EXAMPLE V

HYDROLYTIC REMOVAL OF TRIMETHYLSILYL GROUPS

COMPOUND E

Compound D (0.825 g) was dissolved in 10 ml of THF and cooled at 0° C. An aqueous solution of 3N HCl (3 ml) was added followed by addition of 3 ml hydrogen peroxide (H$_2$O$_2$—30%). The reaction mixture was stirred at 0° C. for 30 minutes, and 100 ml of ether was added. The solution was washed with aqueous NaHCO$_3$ (5%) and then with water. The ether layer was dried (Na$_2$SO$_4$), filtered and evaporated. The residue was dissolved in ether and petroleum ether was added until no further product remains in the mother liquid. This precipitation process is repeated once more to obtain pure product (0.650 g); IR in reciprocal centimeters (CHCl$_3$); 1770,carbonyl of carbonate group; 1720,A-ring carbonyl group; 1630, quinone carbonyl.

EXAMPLE VI

REMOVAL OF BLOCKING GROUP

COMPOUND F

The product of the previous example 0.2 g was dissolved in 1 ml of THF and cooled to 0° C. Glacial acetic acid (2 ml) was added followed by addition of 0.2 g of zinc dust. The mixture was stirred for 30 minutes (The green fluorescent color of the starting material changed to blue). The mixture was filtered and the solid (zinc dust) washed with ether. The combined organic layers were neutralized with an aqueous solution of NaHCO$_3$ (5%) and washed with water. The organic layer was dried (Na$_2$SO$_4$) filtered and evaporated. The residue was redissolved in ether, and petroleum ether was added until none of the desired product remained in the solution. This process was repeated to obtain pure Compound F (0.130 g); IR, CM$^{-1}$(CHCl$_3$); 1720, carbonyl; 1650 and 1620, quinone carbonyl NMR delta ((CD$_3$)$_2$CO); 13.04(1H,S,OH); 11.92 (1H,S,OH).

EXAMPLE VII

GRINGNARD REACTION ON COMPOUND F, FOLLOWED BY OXIDATION

COMPOUNDS G AND H

A solution of compound E (0.11 g) in 25 ml dry THF was added dropwise during 15 min. to a solution of ethynyl magnesium bromide (40 eq) in 50 ml of dry THF at 0° C. The mixture was stirred for an additional 2.25 hr. and then an aqueous solution of tartaric acid and ether were added to quench the reaction. The organic layer was washed with water, dried (Na$_2$SO$_4$), filtered and evaporated. The residue was dissolved in THF and aqueous NaHCO$_3$ (5%) was added at 0° C. After about 1 hour the oxidation was complete. An aqueous solution of tartaric acid and ether were added and the organic layer washed with water, dried (Na$_2$SO$_4$), filtered and evaporated in vacuo. The residue was chromatographed on silica gel (petroleumether-ethyl acetate, 3:1 eluent) to give the desired product.

EXAMPLE IX

AROMATIZATION OF RING D

COMPOUND I

Compound H was dissolved in o-xylene by mild heating and then heated at 140° C. for 30 min. The red color changed to yellow, petroleum ether was added and the precipitate collected and washed with petroleum ether to give the desired product.

EXAMPLE X

PRODUCTION OF DAUNOMYCINONE

To a solution of the product of the previous example in acetone was added HgSO$_4$ and aq. sulfuric acid (H$_2$SO$_4$—40%). The reaction mixture was stirred at 25° C. overnight and ether was added. The organic layer was separated and washed with water, aqueous tartaric acid and water, dried (Na$_2$SO$_4$), filtered and evaporated. The residue was washed with ether-petroleumether to give a mixture of isomers which was converted to the natural product by treatment with trifluoroacetic acid.

The mixture is taken up in trifluoroacetic acid at about 25° C., stirred for 1.3 hours, extracted with ether. The ether layer is neutralized with 5% aqueous NaHCO$_3$; dried (NaSO$_4$), filtered and evaporated in vacuo; the residue washed with 1:1 ether-petroleumether to give the known compound daunomycinone.

What is claimed is:

1. A compound of the formula:

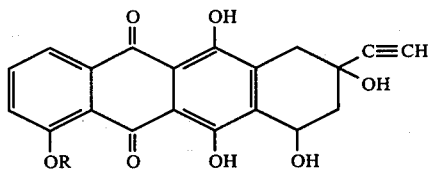

wherein R is an alkyl group containing up to five carbon atoms.

2. A compound of the formula:

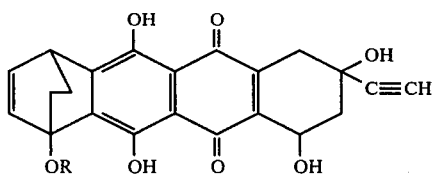

wherein R is an alkyl group containing up to five carbon atoms.

3. A compound of the formula:

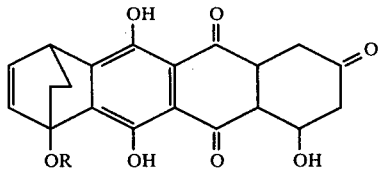

wherein R is an alkyl group containing up to five carbon atoms.

4. A compound of the formula:

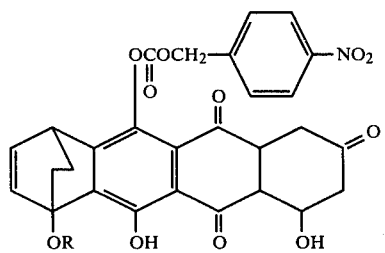

wherein R is an alkyl group containing up to five carbon atoms.

5. A compound of the formula:

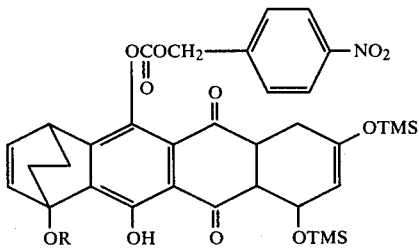

wherein R is an alkyl group containing up to five carbon atoms and TMS is the trimethyl silyl group.

6. A compound of formula:

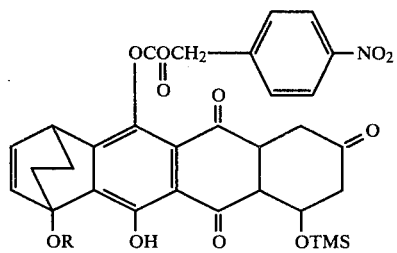

wherein R is an alkyl group containing up to five carbon atom and TMS is the trimethyl silyl group.

7. A compound of the formula:

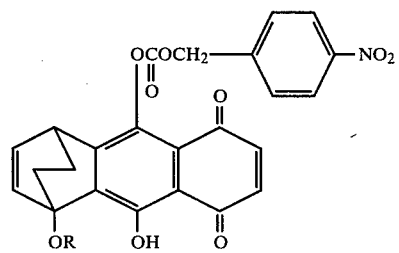

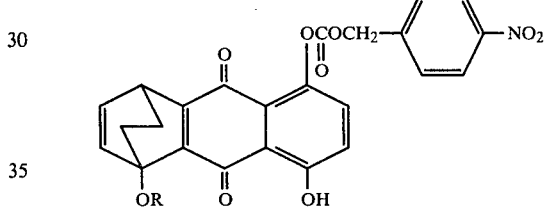

wherein R is an alkyl group containing up to five carbon atoms.

8. A compound of the formula:

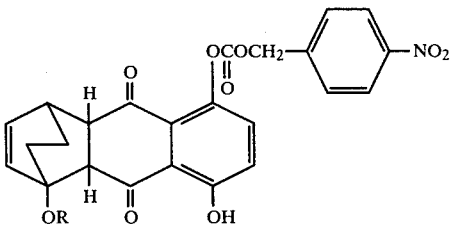

wherein R is an alkyl group containing up to five carbon atoms.

9. A compound of claim 1 wherein R is methyl.
10. A compound of claim 2 wherein R is methyl.
11. A compound of claim 3 wherein R is methyl.
12. A compound of claim 4 wherein R is methyl.
13. A compound of claim 5 wherein R is methyl.
14. A compound of claim 6 wherein R is methyl.
15. A compound of claim 7 wherein R is methyl.
16. A compound of claim 8 wherein R is methyl.

* * * * *

UNITED STATES PATENT AND TRADEMARK OFFICE
CERTIFICATE OF CORRECTION

PATENT NO. : 4,415,498
DATED : November 15, 1983
INVENTOR(S) : T. Ross Kelly, et al.

It is certified that error appears in the above-identified patent and that said Letters Patent are hereby corrected as shown below:

Col. 1, line 36, "25%" should read as --twenty to twenty-five percent--

Col. 3, line 13, "junction" should read --juncture--

Col. 4, line 51, Omit one comma after the word compound.

Signed and Sealed this

Second Day of April 1985

[SEAL]

Attest:

DONALD J. QUIGG

Attesting Officer     Acting Commissioner of Patents and Trademarks